(12) United States Patent
Katagiri et al.

(10) Patent No.: US 6,482,957 B2
(45) Date of Patent: Nov. 19, 2002

(54) CYCLOPENTENECARBOXAMIDE DERIVATIVE, METHOD FOR PREPARING THE SAME AND BICYCLOAMIDE DERIVATIVE USED THEREIN

(75) Inventors: Nobuya Katagiri, Sendai (JP); Chikara Kaneko, Sendai (JP); Junko Sato, Niigata-ken (JP); Masahiro Torihara, Niigata-ken (JP); Koichi Kanehira, Niigata-ken (JP); Yoshin Tamai, Niigata-ken (JP)

(73) Assignee: Kuraray Co., Ltd., Kurashiki (JP)

( * ) Notice: Subject to any disclaimer, the term of this patent is extended or adjusted under 35 U.S.C. 154(b) by 0 days.

(21) Appl. No.: 10/131,244

(22) Filed: Apr. 25, 2002

(65) Prior Publication Data

US 2002/0115857 A1 Aug. 22, 2002

Related U.S. Application Data

(62) Division of application No. 09/613,200, filed on Jul. 11, 2000, which is a division of application No. 09/107,460, filed on Jun. 30, 1998, now Pat. No. 6,127,539, which is a division of application No. 08/748,981, filed on Nov. 14, 1996, now Pat. No. 5,817,812.

(30) Foreign Application Priority Data

Nov. 17, 1995 (JP) .............................. 7-323691
Jul. 9, 1996 (JP) .............................. 8-199652

(51) Int. Cl.[7] .......................................... C07D 209/52
(52) U.S. Cl. ...................... 548/512; 548/412
(58) Field of Search ................. 548/512, 412

(56) References Cited

U.S. PATENT DOCUMENTS

| 5,817,812 A | 10/1998 | Katagiri et al. |
| 6,127,539 A | 10/2000 | Katagiri et al. |

OTHER PUBLICATIONS

Katagiri, et al., "Stereospecific Synthesis of Carbocyclic Nucleosides from 2–Azabicyclo–(2.2.1)Heptan–3–Ones via Sodium Borohydride Mediated Carbon–Nitrogen Bond Cleavage", Tetrahedron Letters, vol. 30, No. 13, pp. 1645–1648, 1989.
Trost, et al., "A Novel Pd–Catalyzed Cycloalkylation to Isoxazoline 2–Oxides. Application for the Asymmetric Syntheses of Carbanucleosides", J. Am. Chem. Soc., vol. 114, No. 22, pp. 8745–8747, 1992.
Gundersen, et al., "Pd(0)–Catalyzed Allylic Alkylation in the Synthesis of (±)Carbovir", Tetrahedron Letters, vol. 33, No. 8, pp. 1085–1088, 1992.
Roberts, et al., "Enzymatic Resolution of cis– and trans–4–Hydroxycyclopent–2–enylmethanol Derivatives and a Novel Preparation of Carbocyclic 2', 3'–Dideoxydidehydronucleosides and Aristeromycin", J. Chem. Soc. Perkin Trans., vol. 1, pp. 2605–2607, 1991.

Ramon, et al., "Nonreductive Enantioselective Ring Opening of N–(Methylsulfonyl)dicarboximides with Diisopropoxytitanium α,α,α',α'–Tetraaryl–1,3–dioxolane–4, 5–dimethanolate", Helvetica Chimica Acta, vol. 79, pp. 875–894, 1996.
Bergmeier, et al., "Chirospecific Synthesis of (1S, 3R)–1–Amino–3–(hydroxymethyl)cyclopentane, a Precursor for Carbocyclic Necleoside Synthesis. Intramolecular Aziridine Cyclizations", J. Org. Chem., vol. 58, pp. 5019–5022, 1993.
Jung, et al., "π–Allylpalladium Formation from Allylic Amines via N,N–Ditosylimides and N–Tosylamides: Efficient Synthesis of the Antiviral Agent Carbovir", J. Org. Chem., vol. 59, pp. 4719–4720, 1994.
Toja, et al., "New Classes of Antimuscarinic Agents Endowed with Selective Antispasmodic Properties", Arzneim.–Forsch./Drug Res., vol. 44, No. 4, pp. 501–509, 1994.
Katagiri, et al., "Synthesis of Novel Nucleosides: Carbocyclic Nucleosides", Tanpakushitsu, Kakusan, Koso, vol. 40, No. 10, pp. 1219–1231, 1995.
Katagiri, et al., "Synthesis of Carbocyclic Nucleosides from 2–Azabicyclo[2,2,1]hept–5–en–3–ones: Sodium Borohydride–Mediated Carbon–Nitrogen Bond Cleavage of Five– and Six–Membered Lactams", Chem. Pharm. Bull., vol. 39, No. 5, pp. 1112–1122, 1991.
Vince, et al., "Synthesis and Anti–HIV Activity of Carbocyclic 2',3'–Didehydro–2',3'–dideoxy2,6–Disubstituted Purine Nucleotides", J. Med. Chem., vol. 33, No. 1, pp. 17–21, 1990.

*Primary Examiner*—Charanjit S Aulakh
(74) *Attorney, Agent, or Firm*—Oblon, Spivak, McClelland, Maier & Neustadt, P.C.

(57) ABSTRACT

A cyclopentenecarboxamide derivative represented by the formula (I):

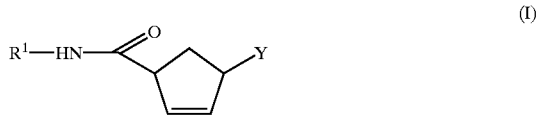

and a method for preparing the cyclopentencarboxamide derivative. A bicycloamide derivative represented by the formula (II):

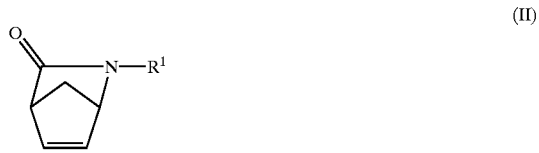

and a method for preparing the bicycloamide derivative.

6 Claims, No Drawings

CYCLOPENTENECARBOXAMIDE DERIVATIVE, METHOD FOR PREPARING THE SAME AND BICYCLOAMIDE DERIVATIVE USED THEREIN

This application is a Div. of Ser. No. 09/613,200 filed Jul. 11, 2000, which is a Div. of Ser. No. 09/107,460 filed Jun. 30, 1998, now U.S. Pat. No. 6,127,539, which is a Div. of Ser. No. 08/748,981 filed Nov. 14, 1996, now U.S. Pat. No. 5,817,812.

BACKGROUND OF THE INVENTION

1. Field of the Invention

The present invention relates to a cyclopentenecarboxamide derivative and its intermediate. More specifically, the present invention relates to a cyclopentenecarboxamide derivative which is useful as an intermediate of a carbocyclic nucleoside usefully used as an anti-viral agent and a bicycloamide derivative which is an intermediate of the cyclopentenecarboxamide derivative, and methods for preparing these compounds.

2. Discussion of the Related Art

Carbocyclic nucleosides are structurally analogous to nucleosides in which the furanose oxygen is replaced by methylene group. Because of the structural resemblance to native nucleosides, carbocyclic nucleosides can behave as substrates or inhibitors of the enzymes which act on nucleosides in living cells. On the other hand, owing to the absence of a glycoside bond, they are not susceptible to the action of hydrolases such as phosphorylases and phosphotransferases that hydrolyze native nucleosides. Also, the metabolic route of carbocyclic nucleosides is different from that of native nucleosides. Because of these differences, carbocyclic nucleosides are endowed with a wide spectrum of biological activities. For example, carbovir, which is represented by the formula (D) set forth later in the present specification, is effective for the therapy and prevention of viral infection [J. Med. Chem., 33, 17 (1990)].

There have been disclosed several methods for preparing a carbocyclic nucleoside, which include the following methods:

(1) Using, as a starting compound, a cycloalkane substituted with an amino group or a cycloalkene substituted with an amino group, a base structure of a nucleic acid base is constructed on the nitrogen atom of the amino group [Protein, nucleic acid, and enzyme, 40, 1219 (1995)];

(2) A purine structure is directly introduced into a 1-alkoxy-2-cyclopentene derivative in the presence of a palladium catalyst [J. Chem. Soc. Parkin Trans. 1, 2605 (1991); Tetrahedron Letters, 33, 1085 (1992); and J. Am. Chem. Soc., 114, 8745 (1992)]; and (3) A purine structure is directly introduced into a 2-cyclopentene-1-yl-N,N-ditosylimide derivative in the presence of a palladium catalyst [J. Org. Chem., 59, 4719(1994)].

All the above methods, however, arise a problem which causes to impair the cost-effectiveness of the production on an industrial scale. In the above method (1), the construct of a nucleic acid structure on the N-atom requires many reaction steps, which in turn increases the production cost. Although the above methods (2) and (3) are advantageous over the method (1) in that a nucleic acid base structure is directly introduced, they require many steps for the synthesis of a cyclopentene derivative used as a starting material.

Therefore, none of the above methods (1) to (3) can be advantageously used for an industrial scale production of a carbocyclic nucleoside.

As a method for preparing an N-sulfonyl derivative of 2-azabicyclo[2.2.1]hept-5-en-3-one, there has been known a method comprising reacting in the presence of sodium hydride at room temperature p-toluenesulfonyl chloride with 2-azabicyclo[2.2.1]hept-5-en-3-one to give N-p-toluenesulfonyl-2-azabicyclo[2.2.1]hept-5-en-3-one [J. Org. Chem. 59, 4719 (1994); and Chem. Pharm. Bull., 39, 1112(1992)].

However, the above method using sodium hydride has a defect of low yield such as 40 to 46% as demonstrated in Comparative Examples described later in the present specification, therefore is not an advantageous method for the industrial production of an N-sulfonyl derivative of 2-azabicyclo[2.2.1]hept-5-en-3-one.

SUMMARY OF THE INVENTION

It is an object of the present invention to provide novel compounds which are usefully employed as intermediates for preparing various carbocyclic nucleosides on an industrial scale and methods for preparing these compounds.

In one embodiment, the present invention relates to a cyclopentenecarboxamide derivative represented by the formula (I):

(I)

wherein $R^1$ is an electron withdrawing group having sulfur atom or phosphorus atom directly bonded to the nitrogen atom of the amido group, and Y is a residue of a substituted or unsubstituted nucleic acid base.

In another embodiment, the present invention relates to a method for preparing a cyclopentenecarboxamide derivative represented by the formula (I):

(I)

wherein $R^1$ is an electron withdrawing group having sulfur atom or phosphorus atom directly bonded to the nitrogen atom of the amido group, and Y is a residue of a substituted or unsubstituted nucleic acid base, comprising the step of:

reacting in the presence of a base and a palladium catalyst, a bicycloamide derivative represented by the formula (II):

(II)

wherein $R^1$ is defined as above, with a compound represented by the formula (III):

Y-H (III)

wherein Y is defined as above.

In still another embodiment, the present invention relates to a method for preparing a cyclopentenecarboxamide derivative represented by the formula (I):

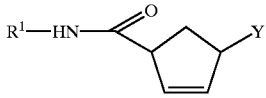 (I)

wherein $R^1$ is an electron withdrawing group having sulfur atom or phosphorus atom directly bonded to the nitrogen atom of the amido group, and Y is a residue of a substituted or unsubstituted nucleic acid base, comprising the steps of:

(A) reacting in the presence of an organolithium compound and at a temperature of from −120° C. to 0° C., 2-azabicyclo[2.2.1]hept-5-en-3-one represented by the formula (IV):

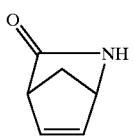 (IV)

with a compound represented by the formula (V):

$R^1$-X (V)

wherein $R^1$ is an electron withdrawing group having sulfur atom or phosphorus atom directly bonded to X, and X is a halogen atom
to yield a bicycloamide derivative represented by the formula (II):

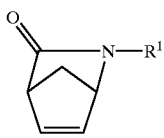 (II)

wherein $R^1$ is defined as above; and
(B) reacting the bicycloamide derivative obtained in the step (A) in the presence of a base and a palladium catalyst with a compound represented by the formula (III):

Y-H (III)

wherein Y is defined as above.

In still another embodiment, the present invention relates to a method for preparing a bicycloamide derivative represented by the formula (II):

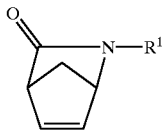 (II)

wherein $R^1$ is an electron withdrawing group having sulfur atom or phosphorus atom directly bonded to the nitrogen atom of the amido group, comprising the step of:
reacting in the presence of an organolithium compound and at a temperature of from −120° C. to 0° C.,
2-azabicyclo[2.2.1]hept-5-en-3-one represented by the formula (IV):

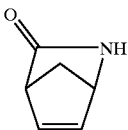 (IV)

with a compound represented by the formula (V):

$R^1$-X (V)

wherein $R^1$ is an electron withdrawing group having sulfur atom or phosphorus atom directly bonded to X, and X is a halogen atom.

The present invention also relates to an N-sulfonylbicycloamide derivative represented by the formula (II-1):

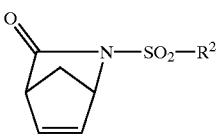 (II-1)

wherein $R^2$ is an aromatic hydrocarbon group which may have a substituent having one or more atoms other than carbon and hydrogen atoms; an N-sulfonylbicycloamide derivative represented by the formula (II-2):

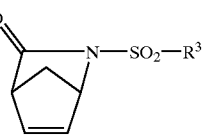 (II-2)

wherein $R^3$ is a substituted or unsubstituted saturated aliphatic hydrocarbon group; and an N-phophorylbicycloamide derivative represented by the formula (II-3):

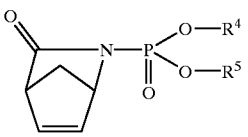 (II-3)

wherein $R^4$ and $R^5$ are independently a substituted or unsubstituted aromatic hydrocarbon group or a substituted or unsubstituted saturated aliphatic hydrocarbon group.

These and other objects of the present invention will be apparent from the following description.

DETAILED DESCRIPTION OF THE INVENTION

The present invention is described in detail below.

As mentioned above, the cyclopentenecarboxamide derivative of the present invention is a compound represented by the formula (I):

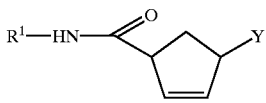 (I)

wherein $R^1$ is an electron withdrawing group having sulfur atom or phosphorus atom directly bonded to the nitrogen atom of the amido group, and Y is a residue of a substituted or unsubstituted nucleic acid base.

The cyclopentenecarboxamide derivative represented by the formula (I) can be obtained by reacting, in the presence of a base and a palladium catalyst, a bicycloamide derivative represented by the formula (II):

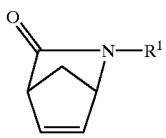 (II)

wherein $R^1$ is defined as above,
with a compound represented by the formula (III):

Y-H (III)

wherein Y is defined as above.

The reaction of the compound represented by the formula (II) with the compound represented by the formula (III) is hereinafter simply referred to as "Reaction I."

In the formulae (I) and (II), $R^1$ is an electron withdrawing group having sulfur atom or phosphorus atom. directly bonded to the nitrogen atom of the amido group in the formulae. Examples of the electron withdrawing groups include sulfonyl group represented by the formula:

$R^6—SO_2—$ and phosphoryl group represented by the formula:

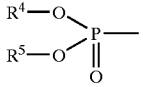

In the above formulae, $R^4$, $R^5$ and $R^6$ independently represent a substituted or unsubstituted aromatic hydrocarbon group or a substituted or unsubstituted saturated aliphatic hydrocarbon group.

In the case where $R^4$, $R^5$ and $R^6$ are a substituted or unsubstituted aromatic hydrocarbon group, those examples include aryl groups such as phenyl, tolyl, biphenyl, terphenyl, naphthyl, anthryl, and phenanthryl groups; aralkyl groups such as benzyl and phenethyl groups. Examples of the substituent which the aromatic hydrocarbon group may have include halogen atoms such as fluorine, chlorine, bromine and iodine atoms; nitro group; alkoxy groups such as methoxy and ethoxy groups; aralkyloxy groups such as benzyloxy group; alkoxycarbonyl groups such as methoxycarbonyl and ethoxycarbonyl groups; cyano group; acyl groups such as acetyl and propionyl groups; silyloxy groups such as trimethylsilyloxy and t-butyldimethylsilyloxy groups; alkoxycarbonyloxy groups such as methoxycarbonyloxy and t-butoxycarbonyloxy groups.

In the case where $R^4$, $R^5$ and $R^6$ are a substituted or unsubstituted saturated aliphatic hydrocarbon group, those examples include alkyl groups such as methyl, ethyl, tert-butyl and hexyl groups; and cycloalkyl groups such as cyclopropyl and cyclohexyl groups. Examples of the substituent which the saturated aliphatic hydrocarbon group may have include halogen atoms such as fluorine, chlorine, bromine and iodine atoms; nitro group; alkoxy groups such as methoxy and ethoxy groups; aralkyloxy groups such as benzyloxy group; alkoxycarbonyl groups such as methoxycarbonyl and ethoxycarbonyl groups; cyano group; acyl groups such as acetyl and propionyl groups; silyloxy groups such as trimethylsilyloxy and t-butyldimethylsilyloxy groups; alkoxycarbonyloxy groups such as methoxycarbonyloxy and t-butoxycarbonyloxy groups.

In formulae (I) and (III), Y is a residue of a substituted or unsubstituted nucleic acid base. The "nucleic acid base" means a constituent base of a nucleoside as defined in the field of nucleic acid chemistry. The term "residue of nucleic acid base" as used herein refers to a residual group formed by removing a hydrogen atom bonded to the nitrogen atom of the N-containing heterocyclic ring of a nucleic acid base from a nucleic acid base. Examples of the nucleic acid bases include purine bases having a purine ring or a deaza analogue thereof, and pyrimidine bases having a pyrimidine ring. The nucleic acid base as mentioned above may have one or more substituents such as halogen atom, alkylamino group, hydroxyl group, alkoxy group and alkylthio group. The substituents can be properly protected by a protecting group.

Concrete examples of the nucleic acid bases include adenine(6-aminopurine), hypoxanthine, guanine(2-amino-6-hydroxypurine), isoguanine, xanthine, 3-deazaadenine, 7-deazaadenine, 2,6-diaminopurine, 6-chloropurine, 2-amino-6-chloropurine and 2-formylamino-6-chloropurine.

In Reaction I, the amount of the compound represented by the formula (III) is 0.5 to 5 times, preferably 0.8 to 2 times the molar amount of the bicycloamide derivative represented by the formula (II).

The base used in Reaction I is not particularly limited. Examples of the base include hydrides of alkali metals such as lithium hydride, sodium hydride and potassium hydride; alkoxides of alkali metals such as sodium t-butoxide, and potassium t-butoxide; alkyl lithiums such as n-butyl lithium and t-butyl lithium; quaternary ammonium hydroxides such as tetrabutylammonium hydroxide and benzyltrimethylammonium hydroxide. The amount of the base used in Reaction I is 0.5 to 2 times, preferably 0.8 to 1.2 times the molar amount of the compound represented by the formula (III).

Examples of the palladium catalyst used in Reaction I include tetrakis(triphenylphosphine)palladium, tetrakis (triethylphosphite)palladium, tris(dibenzylideneacetone) dipalladium, bis(cycloocta-1,5-dien)palladium, di-$\mu$-chlorobis($\eta$-allyl)dipalladium, palladium acetate, palladium chloride, and the like. The amount of the palladium catalyst used in Reaction I is 0.0001 to 1 times, preferably 0.001 to 0.1 times the molar amount of bicycloamide derivative represented by the formula (II).

When a palladium catalyst not having phosphorus ligand is employed, it is desired that the palladium catalyst not having phosphorus ligand is concurrently used together with an organic phosphorus compound. Examples of the organic phosphorus compound include aryl- or alkylphosphines such as triphenylphosphine, tributylphosphine and 1,2-bis (diphenylphosphino)ethane; and aryl- or alkylphosphites such as triethylphosphite and triphenylphosphite. When the organic phosphorus compound has an aromatic ring in its molecule, there may exist a substituent having amino group such as dimethylamino group or diethylaminomethyl group or a substituent having sulfonic acid group in the aromatic ring. The organic phosphorus compound is usually used in an amount of 1 to 100 times the molar amount of palladium catalyst.

It is desired that Reaction I is carried out in the presence of a solvent.

Examples of the solvent include, for instance, hydrocarbons such as toluene and xylene; ethers such as dimethoxyethane and tetrahydrofuran; nitriles such as acetonitrile; amides such as dimethyiformamide, N-methylpyrrolidone and hexamethylphosphoroamide; and sulfur-containing compounds such as sulfolane and dimethylsulfoxide. Those solvents can be used alone or in an admixture thereof. The amount of the solvent is usually 0.1 to 1000 times, preferably 1 to 100 times the amount by weight of the bicycloamide derivative represented by the formula (II).

Reaction I, i.e., the reaction of a bicycloamide derivative represented by the formula (II) with a compound represented by the formula (III) is generally carried out by supplying the bicycloamide derivative represented by the formula (II) and a palladium catalyst to a reaction vessel equipped with a stirrer which is previously charged with the compound represented by the formula (III) and a base. Alternatively, the reaction is carried out by supplying the compound represented by the formula (III) and a base to a reaction vessel equipped with a stirrer which is previously charged with the bicycloamide derivative represented by the formula (II) and a palladium catalyst. The compound represented by the formula (III) and a base may be supplied to the reaction vessel separately or as an admixture thereof.

The reaction temperature is selected from the temperature range of from −50° C. to 180° C., preferably from −20° C. to 120° C. The reaction period of time is usually from 10 minutes to 24 hours.

After the completion of the reaction, the resulting cyclopentenecarboxamide derivative (I) can be isolated from the reaction mixture by a conventional method. For example, the-reaction mixture is added to water, which is then subjected to the extraction with an ester such as ethyl acetate and distilled to obtain a cyclopentenecarboxamide derivative represented by the formula (I).

As occasion demands, the cyclopentenecarboxamide derivative obtained can further be purified by means of column chromatography or recrystallization.

Next, a method for preparing a bicycloamide derivative represented by the formula (II) is explained below. The bicycloamide derivative represented by the formula (II) can be obtained by reacting, in the presence of an organolithium compound and at a temperature of from −120° C. to 0° C., azabicyclo[2.2.1]hept-5-en-3-one represented by the formula (IV):

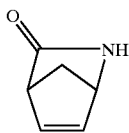

(IV)

with a compound represented by the formula (V):

(V)

wherein $R^1$ is an electron withdrawing group having sulfur atom or phosphorus atom directly bonded to X, and X is a halogen atom. The above reaction is hereinafter simply referred to as "Reaction II."

Both the bicycloamide derivative represented by the formula (II) and 2-azabicyclo[2.2.1]hept-5-en-3-one which is a starting material are unstable compounds. Thus, when the reaction to produce the bicycloamide derivative using 2-azabicyclo[2.2.1]hept-5-en-3-one as a starting material is carried out in the presence of sodium hydride at room temperature as in conventional methods, it is difficult to obtain an objective bicycloamide derivative as represented by the formula (II) in satisfactory yields.

To the contrary, when Reaction II is carried out at a low temperature in the presence of an organolithium compound which allows Reaction II to proceed at low temperatures, it is unexpectedly found that the bicycloamide derivative represented by the formula (II) can be produced in high yields.

Thus, the first characteristic of the method for preparing a bicycloamide derivative of the present invention resides in that Reaction II is carried out at a low temperature of from −120° C. to 0° C. The low temperature can be attained by using a conventional cooling means such as liquid nitrogen or a mixture of dry ice and ethanol.

The second characteristic of the method for preparing a bicycloamide derivative of the present invention is to use an organolithium compound which can effectively catalyze Reaction II even at low temperatures.

The organolithium compounds used in the present invention include, for instance, alkyl lithium compounds such as methyl lithium, n-butyl lithium, and s-butyl lithium, aryl lithium compounds such as phenyl lithium, and the like.

The amount of the organolithium compound is usually 0.5 to 2.0 times, preferably 0.8 to 1.5 times, more preferably 0.9 to 1.2 times the molar amount of 2-azabicyclo[2.2.1]hept-5-en-3-one.

The above reaction is usually carried out in the presence of a solvent. As the solvent, those which do not adversely affect Reaction II can be used. Examples of the solvent usable in the present invention include, for instance, hydrocarbons such as hexane, cyclohexane, heptane, toluene, and xylene; ethers such as dimethoxyethane, diisopropyl ether and tetrahydrofuran. Those solvents can be used alone or in an admixture thereof. The amount of the solvent used varies depending upon the type of solvent and is usually 0.1 to 1000 times, preferably 1 to 100 times the weight of 2-azabicyclo[2.2.1]hept-5-en-3-one.

It is desired that Reaction II is carried out in an atmosphere of inert gas such as nitrogen gas or argon gas. The reaction of 2-azabicyclo[2.2.1]hept-5-en-3-one with a compound represented by the formula (V) is usually carried out by supplying a mixture of 2-azabicyclo[2.2.1]hept-5-en-3-one and an organolithium compound to a reaction vessel equipped with a stirrer which is previously charged with the compound represented by the formula (V). Also, the above reaction can be carried out by supplying the compound represented by the formula (V) to a reaction vessel equipped with a stirrer which is previously charged with 2-azabicyclo [2.2.1]hept-5-en-3-one and an organolithium compound. The compound represented by formula (V) can be used as it is or as a solution of a solvent described above.

The reaction temperature for Reaction II can be selected from the range of from −120° C. to 0° C., preferably from the range of from −90° C. to −30° C.

The duration of Reaction II varies depending upon the reaction conditions employed. The reaction period of time as to Reaction II is usually 10 minutes to 24 hours.

2-Azabicyclo[2.2.1]hept-5-en-3-one is a known compound and can be produced, for example, by the method described in a literature [J. Org. Chem., 39, 564 (1974)]. It is also possible to use an optically active 2-azabicyclo[2.2.1] hept-5-en-3-one.

$R^1$ in the above formula (V) represents the same groups as those represented by $R^1$ in the formulae (I) and (II).

In addition, X in the formula (V) is a halogen atom such as chlorine, bromine or iodine atom.

Examples of compounds represented by the formula (V) are as follows. In the case where $R^1$ is an $R^6$—$SO_2$— group, wherein $R^6$ is an aromatic hydrocarbon, examples thereof include benzenesulfonyl chloride, toluenesulfonyl chloride, p-methoxybenzenesulfonyl chloride, o-methoxybenzenesulfonyl chloride, o-nitrobenzenesulfonyl chloride, p-nitrobenzenesulfonyl chloride, p-chlorobenzenesulfonyl chloride, o-chlorobenzenesulfonyl chloride, p-bromobenzenesulfonyl chloride, p-fluorobenzenesulfonyl chloride, 2,5-dichlorobenzenesulfonyl chloride, and the like.

Also, in the case where $R^1$ is an $R^6$—$SO_2$— group, wherein $R^6$ is an aliphatic hydrocarbon, examples thereof include methanesulfonyl chloride, trifluoromethanesulfonyl chloride, ethanesulfonyl chloride, β-chloroethanesulfonyl chloride, tert-butanesulfonyl chloride, n-hexanesulfonyl chloride, cyclopropanesulfonyl chloride, cyclohexanesulfonyl chloride, and the like.

In the case where $R^1$ is a group represented by the formula:

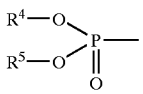

wherein $R^4$ and $R^5$ are as defined above, examples thereof include dimethylphosphoryl chloride, diethylphosphoryl chloride, dibutylphosphoryl chloride, diphenylphosphoryl chloride, ditolylphosphoryl chloride, and the like.

The compound represented by the formula (V) is usually used in an amount of from 0.5 to 2.0 times, preferably from 0.9 to 1.2 times the molar amount of 2-azabicyclo[2.2.0]hept-5-en-3-one represented by the formula (IV).

After the reaction is completed, the separation and purification of the bicycloamide derivative represented by the formula (II) are carried out by a known method. For instance, the reaction mixture is neutralized with acetic acid, dilute sulfuric acid or aqueous ammonium chloride solution. Thereafter, the resultant neutralized solution is extracted with an organic solvent such as ethyl acetate, chloroform or toluene. The solvent is then distilled off from the resultant extractant to isolate a bicycloamide derivative represented by the formula (II). Also, the resultant bicycloamide derivative is further purified by such a purification method as column chromatography or recrystallization as occasion demands.

According to the method of the present invention, the bicycloamide derivative represented by the formula (II) is obtained in a high yield.

Typical examples of the above bicycloamide derivative include the following:

(i) N-Sulfonylbicycloamide derivative represented by the formula (II-1):

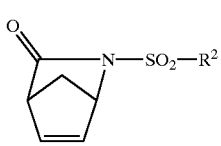

wherein $R^2$ is an aromatic hydrocarbon group which may have a substituent containing one or more atoms except carbon and hydrogen atoms;

(ii) N-Sulfonylbicycloamide derivative represented by the formula (II-2):

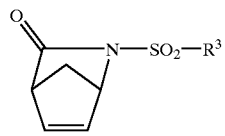

wherein $R^3$ is a substituted or unsubstituted saturated aliphatic hydrocarbon group; and (iii) N-Phosphorylbicycloamide derivative represented by the formula (II-3):

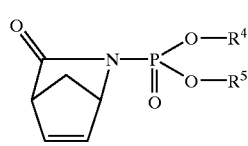

wherein $R^4$ and $R^5$ are independently a substituted or unsubstituted aromatic hydrocarbon group or a substituted or unsubstituted saturated aliphatic hydrocarbon group.

In the N-sulfonylbicycloamide derivative represented by the formula (II-1), $R^2$ is an aromatic hydrocarbon group which may have a substituent containing one or more atoms except carbon and hydrogen atoms. Representative examples of the aromatic hydrocarbon group are, for instance, aryl groups such as phenyl, naphthyl, anthryl, and phenanthryl groups; aralkyl groups such as benzyl and phenethyl groups, and the like. Those groups may have a substituent containing one or more atoms except carbon and hydrogen atoms. Examples of the substituents containing one or more atoms except carbon and hydrogen atoms include halogen atoms such as fluorine, chlorine, bromine and iodine; nitro group; alkoxy groups such as methoxy and ethoxy groups; aralkyloxy groups such as benzyloxy group; alkoxycarbonyl groups such as methoxycarbonyl and ethoxycarbonyl groups; cyano group; acyl groups such as acetyl and propionyl groups; silyloxy groups such as trimethylsilyloxy and tert-butyldimethylsilyloxy groups; alkoxycarbonyloxy groups such as methoxycarbonyloxy, and tert-butoxycarbonyloxy groups, and the like.

In the N-sulfonylbicycloamide derivative represented by the formula (II-2), $R^3$ is a substituted or unsubstituted saturated aliphatic hydrocarbon group. Examples of the substituted or unsubstituted saturated aliphatic hydrocarbon groups include, for instance, alkyl groups such as methyl, ethyl, tert-butyl and hexyl groups; cycloalkyl groups such as cyclopropyl and cyclohexyl groups, and the like. Examples of the substituents include, for instance, halogen atoms such as fluorine, chlorine, bromine and iodine atoms; nitro group; alkoxy groups such as methoxy and ethoxy groups; aralkyloxy groups such as benzyloxy group; alkoxycarbonyl groups such as methoxycarbonyl and ethoxycarbonyl groups; cyano group; acyl groups such as acetyl and propionyl groups; silyloxy groups such as trimethylsilyloxy and tert-butyldimethylsilyloxy groups; alkoxycarbonyloxy groups such as methoxycarbonyloxy and tert-butoxycarbonyloxy groups, and the like.

In the N-phosphorylbicycloamide derivative represented by the formula (II-3), $R^4$ and $R^5$ are defined as above.

Here, examples of the N-sulfonylbicycloamide derivative represented by the formula (II-1) include the following:

2-(N-benzenesulfonyl)-2-azabicyclo[2.2.1]-hept-5-en-3-one;

2-(N-o-nitrobenzenesulfonyl)-2-azabicyclo[2.2.1]-hept-5-en-3-one;

2-(N-p-nitrobenzenesulfonyl)-2-azabicyclo[2.2.1]-hept-5-en-3-one;

2-(N-p-chlorobenzenesulfonyl)-2-azabicyclo[2.2.1]-hept-5-en-3-one;

2-(N-o-chlorobenzenesulfonyl)-2-azabicyclo[2.2.1]-hept-5-en-3-one;

2-(N-p-bromobenzenesulfonyl)-2-azabicyclo[2.2.1]-hept-5-en-3-one;

2-(N-p-fluorobenzenesulfonyl)-2-azabicyclo[2.2.1]-hept-5-en-3-one;

2-(N-p-methoxybenzenesulfonyl)-2-azabicyclo[2.2.1]-hept-5-en-3-one;

2-(N-o-methoxybenzenesulfonyl)-2-azabicyclo[2.2.1]-hept-5-en-3-one; and 2-(N-2,5-dichlorobenzenesulfonyl)-2-azabicyclo[2.2.1]-hept-5-en-3-one.

In addition, examples of the N-sulfonylbicycloamide derivative represented by the formula (II-2) include the following:

2-(N-methanesulfonyl)-2-azabicyclo[2.2.1]-hept-5-en-3-one;

2-(N-trifluoromethanesulfonyl)-2-azabicyclo[2.2.1]-hept-5-en-3-one;

2-(N-ethanesulfonyl)-2-azabicyclo[2.2.1]-hept-5-en-3-one;

2-(N-β-chloroethanesulfonyl)-2-azabicyclo[2.2.1]-hept-5-en-3-one;

2-(N-tert-butanesulfonyl)-2-azabicyclo[2.2.1]-hept-5-en-3-one;

2-(N-n-hexanesulfonyl)-2-azabicyclo[2.2.1]-hept-5-en-3-one;

2-(N-cyclopropanesulfonyl)-2-azabicyclo[2.2.1]-hept-5-en-3-one; and 2-(N-cyclohexanesulfonyl)-2-azabicyclo[2.2.1]-hept-5-en-3-one.

In addition, examples of the N-phosphorylbicycloamide derivative represented by the formula (II-3) include the following:

2-(N-dimethylphosphoryl)-2-azabicyclo[2.2.1]-hept-5-en-3-ene;

2-(N-diethylphosphoryl)-2-azabicyclo[2.2.1]-hept-5-en-3-one;

2-(N-dibutylphosphoryl)-2-azabicyclo[2.2.1]-hept-5-en-3-one;

22-(N-diphenylphosphoryl)-2-azabicyclo[2.2.1]-hept-5-en-3-one; and 2-(N-ditolylphosphoryl)-2-azabicyclo[2.2.1]-hept-5-en-3-one.

The cyclopentenecarboxamide derivative thus obtained is useful as an intermediate for synthesizing various anti-viral agents.

The reaction according to the present invention can be represented by the following reaction scheme (I):

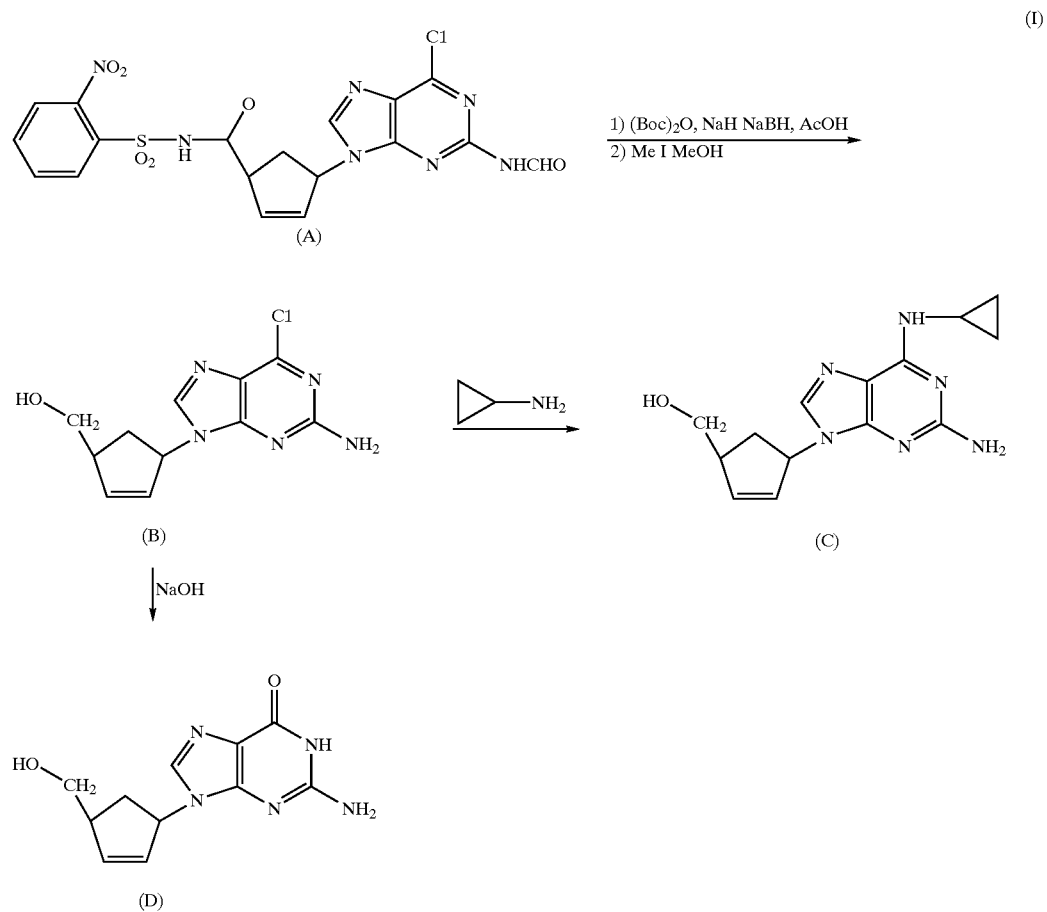

In the reaction scheme (I), for example, a product obtained by the present invention is compound (A), where $R^1$ in the formula (I) is an o-nitrobenzene sulfonyl group and Y is 2-formyl-amino-6-chloropurine-4-yl group. From the compound (A), the compound (B) is synthesized by the steps of protecting the amino group at the 2-position, N-methylating the amido group, reducing with sodium boron hydride in methanol, and de-protecting. A carbocyclic nucleoside derivative having anti-viral activity (C) can be obtained by reacting the compound (B) with a cyclopropylamine according to the method disclosed in JP-A-2-45486. Also, carbovir(D) having anti-viral activity can be obtained by treating the compound (B) with an alkali according to the method described in J. Org. Chem. 59, 4719 (1994).

EXAMPLES

The present invention is hereinafter described in more detail by means of the following working examples, which are not to be construed as limitative.

Example 1

Preparation of 2-(N-o-Nitrobenzenesulfonyl)-2-azabicyclo[2.2.1]hept-5-en-3-one

The amount 1.09 g (10 mmol) of 2-azabicyclo[2.2.1]hept-5-en-3-one was dissolved in 31 ml of tetrahydrofuran, to which 6.41 ml of 1.56 M n-hexane solution of n-butyl lithium (corresponding to 10 mmol of n-butyl lithium) was added under argon atmosphere at a temperature of from −75° C. to −70° C., and stirred for about 30 minutes with maintaining its temperature. To the resultant mixture, a solution obtained by dissolving 2.44 g (11 mmol) of o-nitrobenzenesulfonyl chloride in 4 ml of tetrahydrofuran was added dropwise at a temperature of from −75° C. to −70° C. over one hour period, which was then stirred at −75° C. for about 2 hours. The resultant reaction mixture was neutralized by adding 0.12 g (2 mmol) of acetic acid and diluted with 50 ml of toluene, which was then washed with 50 ml of 10% by weight of a saline solution. The solvent of the resultant mixture was distilled off under reduced pressure to yield 2-(N-o-Nitrobenzensulfonyl)-2-azabicyclo[2.2.1]hept-5-en-3-one in an amount of 2.44 g (8.3 mmol). The yield was 83% by mole.

The physical properties of the compound thus obtained were as follows:

$^1$H-NMR (CDCl$_3$, 300 MHz) δ (ppm): 2.32(1H, m), 2.58(1H, d), 3.44(1H, m), 5.23(1H, m), 6.66(1H, m), 7.04 (1H, m), 7.78(3H, m), 8.35(1H, m).

Example 2

Preparation of 2-(N-p-Toluenesulfonyl)-2-azabicyclo[2.2.1]hept-5-en-3-one

The amount 1.09 g (10 mmol) of 2-azabicyclo[2.2.1]hept-5-en-3-one was dissolved in 20 ml of tetrahydrofuran, to which 7.50 ml of 1.60 M n-hexane solution of n-butyl lithium (corresponding to 12 mmol of n-butyl lithium) was added under argon atmosphere at a temperature of −75° C., and stirred for about one hour with maintaining its temperature. To the resultant mixture, 2.29 g (12 mmol) of p-toluenesulfonyl chloride was added and stirred at −75° C. for about 3.5 hours. To the resultant reaction mixture, 20 ml of 5% by weight aqueous sulfuric acid was added, which was extracted with 40 ml of ethyl acetate. The organic layer thus obtained was washed with 20 ml of a saturated aqueous solution of sodium bicarbonate and then with 20 ml of saturated saline solution. The solvent of the resultant mixture was distilled off under reduced pressure to yield 2-(N-p-toluenesulfonyl)-2-azabicyclo[2.2.1]hept-5-en-3-one in an amount of 2.89 g (8.0 mmol). The yield was 80% by mole.

The physical properties of the compound thus obtained were as follows:

$^1$H-NMR (CDCl$_3$, 300 MHz) δ (ppm): 2.42(5H, m), 3.37(1H, m), 5.04(1H, m), 6.37(1H, m), 6.64(1H, dd, J=5.3 Hz, 2.1 Hz), 7.28(2H, d, J=8.1 Hz), 7.79(2H, d, J=8.3 Hz).

Example 3

Preparation of 2-(N-Benzenesulfonyl)-2-azabicyclo[2.2.1]hept-5-en-3-one

The amount 1.09 g (10 mmol) of 2-azabicyclo[2.2.1]hept-5-en-3-one was dissolved in 20 ml of tetrahyarofuran, to which 7.50 ml of 1.60 M n-hexane solution of n-butyl lithium (corresponding to 12 mmol of n-butyl lithium) was added under argon atmosphere at a temperature of −75° C., and stirred for about one hour with maintaining its temperature. To the resultant mixture, 2.12 g (12 mmol) of benzenesulfonyl chloride was added and stirred at −75° C. for about 3.5 hours. To the resultant reaction mixture, 20 ml of 5% by weight aqueous sulfuric acid was added, which was extracted with 40 ml of ethyl acetate. The solvent was distilled off and the residue thus obtained was purified by silica gel column chromatography using a mixture of hexane and ethyl acetate (volume ratio: 2:1) as a developing solvent to yield 2-(N-benezenesulfonyl)-2-azabicyclo[2.2.1]hept-5-en-3-one in an amount of 1.82 g (7.3 mmol). The yield was 73% by mole.

The physical properties of the compound thus obtained were as follows:

$^1$H-NMR (CDCl$_3$, 300 MHz) δ (ppm): 2.18(1H, m), 2.43(1H, d), 3.39(1H, m), 5.05(1H, m), 6.37(1H, m), 6.62 (1H, m), 7.56(3H, m), 7.92(2H, m).

Example 4

Preparation of 2-(N-p-Chlorobenzenesulfonyl)-2-azabicyclo[2.2.1]hept-5-en-3-one

The amount 6.46 g (50 mmol) of 2-azabicyclo[2.2.1]hept-5-en-3-one was dissolved in 100 ml of tetrahydrofuran, to which 37.50 ml of 1.60 M n-hexane solution of n-butyl lithium (corresponding to 60 mmol of n-butyl lithium) was added under argon atmosphere at a temperature of −75° C., and stirred for about one hour with maintaining its temperature. To the resultant mixture, 12.66 g (60 mmol) of p-chlorobenzenesulfonyl chloride was added and stirred at −75° C. for about 3 hours. To the resultant reaction mixture, 40 ml of 5% by weight aqueous sulfuric acid was added, which was extracted with 100 ml of ethyl acetate. The organic layer thus obtained was washed with 40 ml of a saturated aqueous solution of sodium bicarbonate and then with 40 ml of saturated saline solution. The solvent of the resultant mixture was distilled off under reduced pressure. The residue thus obtained was purified by silica gel column chromatography using a mixture of hexane and ethyl acetate (volume ratio: 2:1) as a developing solvent, and by recrystallization in diisopropyl ether to yield 2-(N-p-chlorobenzenesulfonyl)-2-azabicyclo[2.2.1]hept-5-en-3-one in an amount of 9.79 g (34.5 mmol). The yield was 69% by mole.

The physical properties of the compound thus obtained were as follows:

$^1$H-NMR (CDCl$_3$, 300 MHz) δ (ppm): 2.21(1H, m), 2.44(1H, d), 3.40(1H, m), 5.06(1H, m), 6.41(1H, m), 6.67 (1H, m), 7.47(2H, m), 7.85(2H, m).

Example 5

Preparation of 2-(N-2,5-Dichlorobenzenesulfonyl)-2-azabicyclo[2.2.1]hept-5-en-3-one The same procedures as in Example 4 were carried out except that 15.03 g (60 mmol) of 2,5-dichlorobenzenesulfonyl chloride was used instead of 12.66 g (60 mmol) of p-chlorobenzenesulfonyl chloride. The residue obtained by distilling off the solvent was purified by recrystallization in a mixture of diisopropyl ether and ethyl acetate to yield 2-(N-2,5-dichlorobenezenesulfonyl)-2-azabicyclo[2.2.1]hept-5-en-3-one in an amount of 11.89 g (37.5 mmol). The yield was 75% by mole.

The physical properties of the compound thus obtained were as follows:

$^1$H-NMR (CDCl$_3$, 300 MHz) δ (ppm): 2.27(1H, d), 2.53 (1H, d), 3.44(1H, m), 5.23(1H, m), 6.69(1H, m), 6.99(1H, m), 7.48(2H, m), 8.19(1H, d).

Example 6

Preparation of 2-(N-p-Methoxybenzenesulfonyl)-2-azabicyclo[2.2.1]hept-5-en-3-one The same procedures as in Example 4 were carried out except that 12.40 g (60 mmol) of p-methoxybenzenesulfonyl chloride was used instead of 12.66 g (60 mmol) of p-chlorobenzenesulfonyl chloride. The residue obtained by distilling off the solvent was purified by silica gel column chromatography using a mixture of hexane and ethyl acetate (volume ratio: 3:1) as a developing solvent, and by recrystallization in diisopropyl ether to yield 2-(N-p-methoxybenzenesulfonyl)-2-azabicyclo[2.2.1]hept-5-en-3-one in an amount of 8.66 g (31.0 mmol). The yield was 62% by mole.

The physical properties of the compound thus obtained were as follows:

$^1$H-NMR (CDCl$_3$, 300 MHz) δ (ppm): 2.17(1H, m), 2.43(1H, m), 3.37(1H, m), 3.87(3H, s), 5.03(1H, m), 6.36 (1H, m), 6.63(1H, m), 6.94(2H, m), 7.83(2H, m).

Example 7

Preparation of 2-(N-p-Nitrobenzenesulfonyl)-2-azabicyclo[2.2.1]hept-5-en-3-one

The same procedures as in Example 4 were carried out except that 13.30 g (60 mmol) of p-nitrobenzenesulfonyl chloride was used instead of 12.66 g (60 mmol) of p-chlorobenzenesulfonyl chloride. The residue obtained by distilling off the solvent was purified by recrystallization twice in the mixture of diethyl ether and ethyl acetate to yield 2-(N-p-nitrobenzenesulfonyl)-2-azabicyclo[2.2.1]hept-5-en-3-one in an amount of 10.45 g (35.5 mmol). The yield was 71% by mole.

The physical properties of the compound thus obtained were as follows:

$^1$H-NMR (CDCl$_3$, 300 MHz) δ (ppm): 2.22(1H, m), 2.43(1H, m), 3.39(1H, m), 5.07(1H, m), 6.40(1H, m), 6.68 (1H, m), 8.08(2H, m), 8.26(2H, m).

Example 8

Preparation of 2-(N-Trifluoromethanesulfonyl)-2-azabicyclo[2.2.1]hept-5-en-3-one The amount 1.09 g (10 mmol) of 2-azabicyclo[2.2.1]hept-5-en-3-one was dissolved in 31 ml of tetrahydrofuran, to which 6.41 ml of 1.56 M n-hexane solution of n-butyl lithium (corresponding to 10 mmol of n-butyl lithium) was added under argon atmosphere at a temperature of from −75° C. to −70° C. and stirred for about 30 minutes with maintaining its temperature. To the resultant mixture, a solution obtained by dissolving 1.85 g (11 mmol) of trifluoromethanesulfonyl chloride in 4 ml of tetrahydrofuran was added dropwise at a temperature of from −75° C. to −70° C. over one hour period, which was then stirred at −75° C. for about 2 hours. The resultant reaction mixture was neutralized by adding 0.12 g (2 mmol) of acetic acid and diluted with 50 ml of ethyl acetate, which was then washed with 50 ml of 10% by weight saline solution. The solvent of the resultant mixture was distilled off under reduced pressure to yield 2-(N-trifluoromethanesulfonyl)-2-azabicyclo[2.2.1]hept-5-en-3-one in an amount of 1.72 g (7.5 mmol). The yield was 75% by mole.

The physical properties of the compound thus obtained were as follows:

$^1$H-NMR (CDCl$_3$, 300 MHz) δ (ppm): 2.24(1H, m), 2.45(1H, m), 3.41(1H, m), 5.03(1H, m), 6.38(1H, m), 6.65 (1H, m).

Example 9

Preparation of 2-(N-Diphenylphophoryl)-2-azabicyclo[2.2.1]hept-5-en-3-one

The amount 1.05 g (9.6 mmol) of 2-azabicyclo[2.2.1]hept-5-en-3-one was dissolved in 20 ml of tetrahydrofuran, to which 6.73 ml of 1.56 M n-hexane solution of n-butyl lithium (corresponding to 10.5 mmol of n-butyl lithium) was added under argon atmosphere at a temperature of −78° C. and stirred for about 30 minutes with maintaining its temperature. The resultant mixture was added dropwise to a solution obtained by dissolving 2.17 ml (10.5 mmol) of diphenylphosphoryl chloride in 10 ml of tetrahydrofuran with ace-cooling, which was then stirred for about 5 minutes. To the resultant reaction mixture, a saturated aqueous solution of ammonium chloride was added with ice-cooling, which was extracted with ethyl acetate. The organic layer thus obtained was dried over magnesium sulfate and the solvent of the resultant mixture was distilled off under reduced pressure. The residue thus obtained was purified by silica gel column chromatography using a mixture of hexane and ethyl acetate (volume ratio: 3:1) as a developing solvent, and by recrystallization in a mixture of hexane and ethyl acetate to yield 2-(N-diphenylphosphoryl)-2-azabicyclo[2.2.1]hept-5-en-3-one in an amount of 2.12 g. The yield was 88% by mole.

The physical properties of the compound thus obtained are as follows:

Melting point: 51° C. $^1$H-NMR (CDCl$_3$, 300 MHz) δ (ppm): 2.08–2.18(2H, m), 3.34–3.36(1H, m), 4.86–4.92(1H, m), 6.45–6.56(2H, m), 7.14–7.40(10H, m).

Example 10

Preparation of (±)-2-Formylamino-6-chloro-9-[c-4-(N-o-nitrobenzenesulfonyl)carbamoylcyclopent-2-en-γ-1-yl]-9H-purine The amount 2.63 g (6.0 mmol) of tetrabutylammonium salt of 2-formylamino-6-chloropurine which was prepared from 2-formylamino-6-chloropurine and tetrabutylammonium hydroxide was dissolved in 20 ml of tetrahydrofuran, to which 56.0 mg (0.25 mmol) of palladium acetate and 360 mg (1.75 mmol) of triisopropyl phosphate were added and stirred under nitrogen atmosphere at a temperature of 50° C. for 30 minutes. To the resultant mixture, 1.47 g (5.0 mmol) of 2-(N-o-nitrobenzenesulfonyl)-2-azabicyclo[2.2.1]hept-5-en-3-one obtained in Example 1 was added dropwise at room temperature over a period of 2 hours, which was then stirred for one hour. The resultant reaction mixture was neutralized with acetic acid, and the solvent of the resultant mixture was distilled off under reduced pressure. The residue thus obtained was purified by silica gel column chromatography using a mixture of chloroform and methanol (volume ratio: 15:1) as a developing solvent to yield (±)-2-formylamino-6-chloro-9-[c-4-(N-o-nitrobenzenesulfonyl) carbamoylcyclopent-2-en-γ-1-yl]-9H-purine in an amount of 1.11 g. The yield was 45% by mole.

The physical properties of the compound thus obtained were as follows:

$^1$H-NMR (DMSO-$d_6$, 300 MHz) δ (ppm): 1.89(1H, ddd, J=14.0 Hz, 5.0 Hz, 5.0 Hz), 2.52(1H, ddd, J=14.0 Hz, 8.9 Hz, 8.9 Hz), 3.53(1H, m), 5.36(1H, m), 5.85(1H, m), 5.93 (1H, m), 7.6–7.8(3H, m), 7.85(1H, s), 7.9–8.0(1H, m), 9.08(1H, d, J=9.5 Hz), 10.94(1H, d, J=9.5 Hz), 12.35(1H, brs); High resolution mass spectrometry: m/z;

| $C_{18}H_{14}ClN_7O_6S(M^+)$ | Calculated value: 491.8714 |
|---|---|
| | Found value: 491.5225 |

Example 11

Preparation of (±)-6-Chloro-9-[c-4-(N-p-toluenesulfonyl)carbamoylcyclopent-2-en-γ-yl]-9H-purine The amount 48 mg (1.2 mmol) of sodium hydride (60% by weight mineral oil solution) was suspended in 4 ml of dimethylformamide, to which a solution prepared by dissolving 154 mg (1 mmol) of 6-chloropurine in 4 ml of dimethylformamide was added dropwise and stirred for 30 minutes at 60° C. To the resultant mixture, a solution prepared by dissolving 115.6 mg (0.1 mmol) of tetrakis (triphenylphosphine) palladium in 4 ml of anhydrous tetrahydrofuran was added dropwise, to which a solution prepared by dissolving 131.5 mg (0.5 mmol) of 2-(N-p-toluenesulfonyl)-2-azabicyclo[2.2.1]hept-5-en-3-one obtained in Example 2 in 4 ml of dimethylformamide was added dropwise and stirred for 30 minutes with maintaining its temperature. The resultant reaction mixture was neutralized with acetic acid and the solvent was distilled off under reduced pressure. The residue thus obtained was purified by silica gel column chromatography using a mixture of hexane and ethyl acetate (volume ratio: 1:3) as a developing solvent to yield (±)-6-chloro-9-[c-4-(N-p-toluenesulfonyl) carbamoylcyclopent-2-en-γ-1-yl]-9H-purine in an amount of 97 mg. The yield was 47% by mole.

The physical properties of the compound thus obtained were as follows:

Melting point: 243° C. $^1$H-NMR (DMSO-$d_6$, 500 MHz) δ (ppm): 2.04(1H, dt, J=14.3 Hz, 4.8 Hz), 2.38(3H, s), 2.75 (1H, dt, J=14.3 Hz, 8.8 Hz), 3.70(1H, m), 5.73(1H, m), 6.10(1H, m), 6.18(1H, m), 7.39(2H, d), 7.79(2H, d), 8.31 (1H, s), 8.75(1H, s), 12.35(1H, s); High resolution mass spectrometry: m/z;

| $C_{18}H_{16}ClN_5O_3S(M^+)$ | Calculated value: 417.0663 |
|---|---|
| | Found value: 417.0635 |

Example 12

Preparation of (±)-2-Amino-6-chloro-9-[c-4-(N-p-toluenesulfonyl)carbamoylcyclopent-2-en-γ-1-yl]-9H-purine To 131.5 mg (0.5 mmol) of 2-(N-p-toluenesulfonyl)-2-azabicyclo[2.2.1]hept-5-en-3-one obtained in Example 2, 205.29 mg (0.5 mmol) of tetrabutylammonium salt of 2-amino-6-chloropurine prepared from 2-amino-6-chloropurine and tetrabutylammonium hydroxide, 115.5 mg (0.1 mmol) of tetrakis(triphenylphosphine) palladium and 6 ml of dimethylformamide were added under argon atmosphere, and the resultant mixture was stirred at room temperature for 24 hours. The resultant reaction mixture was neutralized with acetic acid, and the solvent was distilled off under reduced pressure. The residue thus obtained was purified by silica gel column chromatography using a mixture of chloroform and methanol(volume ratio of 12:1) to yield (±)-2-amino-6-chloro-9-[c-4-(N-p-toluenesulfonyl) carbamoylcyclopent-2-en-γ-1-yl]-9H-purine in an amount of 67 mg. The yield was 31% by mole.

The physical properties of the compound thus obtained were as follows:

$^1$H-NMR (DMSO-$d_6$, 500 MHz, δ ppm): 1.92(1H, dt, J=14.3 Hz, 5.1 Hz), 2.38(3H, s), 2.65(1H, dt, J=14.3 Hz, 9.2 Hz), 3.64(1H, m), 5.43(1H, m), 6.01(1H, m), 6.12(1H, m), 6.89(2H, s), 7.38(2H, d, J=8.0 Hz), 7.78(2H, d, J=8.0 Hz), 8.30(1H, s), 12.35(1H, brs); High resolution mass spectrometry: m/z;

| $C_{18}H_{17}ClN_6O_3S(M^+)$ | Calculated value: 432.0768 |
|---|---|
| | Found value: 432.0777 |

Example 13

Preparation of (±)-6-Chloro-9-[c-4-(N-diphenylphosphoryl)carbamoylcyclopent-2-en-γ-1-yl]-9H-purine The amount 22 mg (0.55 mmol) of sodium hydride (60% by weight mineral oil solution) was suspended in 1 ml of N-methylpyrrolidone, to which a solution prepared by dissolving 85 mg (0.55 mmol) of 6-chloropurine in 1 ml of N-methylpyrrolidone was added dropwise at 0° C. under argon atmosphere, and stirred at 60° C. for one hour. To the resultant mixture, a solution prepared by dissolving 11 mg (0.05 mmol) of palladium acetate in 0.5 ml of anhydrous tetrahydrofuran and 0.074 ml(0.3 mmol) of triisopropylphosphite were added dropwise with ice-cooling, to which a solution prepared by dissolving 163 mg (0.5 mmol) of 2-(N-diphenylphosphoryl)-2-azabicyclo[2.2.1]hept-5-en-3-one obtained in Example 9 in 1 ml of N-methylpyrrolidone was added dropwide and stirred for one hour at room temperature. The resultant reaction mixture was neutralized with acetic acid, and the solvent was distilled off under reduced pressure. The residue thus obtained was purified by silica gel column chromatography using a mixture of hexane and ethyl acetate (volume ratio: 1:5) to yield (±)-6-chloro- 9-[c-4-(N-diphenylphophoryl)carbamoylcyclopent-2-en-γ-1-yl ]-9H-purine in an amount of 137 mg. The yield was 55% by mole.

The physical properties of the compound thus obtained were as follows:

$^1$H-NMR (DMSO-d$_6$, 300 MHz, δ ppm): 2.22(1H, dt, J=5.22 Hz, 15.11 Hz), 2.92(1H, dt, J=9.62 Hz, 15.11 Hz), 3.66–3.77(1H, m), 5.66–5.75(1H, m), 5.87(1H, dt, J=2.20 Hz, 5.50 Hz), 5.98(1H, dt, J=2.20 Hz, 5.22 Hz), 7.10–7.34 (10H, m), 8.16(1H, s), 8.93(1H, s), 9.80–9.83(1H, m); High resolution mass spectrometry: m/z;

| $C_{23}H_{19}ClN_5O_4P(M^+)$ | Calculated value: 495.0863 |
|---|---|
| | Found value: 495.0878 |

REFERENCE EXAMPLE 1

Preparation of (±)-2-Amino-6-chloro-9-[c-4-hydroxymethylcyclopent-2 -en-γ-1-yl]-9H-purine (Compound B)

(1) The amount 440 mg (11.0 mmol) of sodium hydride (60% by weight mineral oil solution) was suspended in 50 ml of anhydrous tetrahydrofuran, to which 2.46 g (5.0 mmol) of (±)-2-formylamino-6-chloro-9-[c-4-(N-o-nitrobenzensulfonyl)carbamoylcyclopent-2-en-γ-1-yl]-9H-purine obtained in Example 10 was added and stirred for one hour with ice-cooling. To the resultant mixture, 2.18 g (10.0 mmol) of ditert-butyl dicarbonate was added and stirred at room temperature for 2 hours and then at 50° C. for 3 hours. After cooling, 7.60 g (50 mmol) of methyl iodide was added to the resultant mixture and stirred overnight. The resultant mixture was added to water and extracted with ethyl acetate. After the organic layer was washed with saturated saline solution, the solvent was distilled off under reduced pressure to yield 5.51 g of a crude product of (±)-2-(N-tert-butoxycarbonyl-N-formyl) amino-6-chloro-9-[c-4-(N-methyl-N-o-nitrobenzenesulfonyl)carbamoylcyclopent-2-en-γ-1-yl]-9H-purine. This crude product was used in the next reaction without purification.

(2) The crude product obtained in the above (1) was dissolved in 100 ml of methanol and cooled to −20° C., to which 0.19 g (5.0 mmol) of sodium borohydride was added in small portions with maintaining the internal temperature below 0° C. The resultant mixture was stirred at room temperature for 8 hours and neutralized with 5% by weight aqueous solution of sulfuric acid. Then the solvent was distilled off under reduced pressure. Water was added to the residue thus obtained, which was extracted with ethyl acetate. The organic layer was concentrated under reduced pressure to yield a crude product in an amount of 5.8 g.

(3) The crude product obtained in the above (2) was dissolved in 10 ml of 90% by weight aqueous solution of acetic acid and stirred at 50° C. for 8 hours. After cooling, the solvent was distilled off under reduced pressure. The residue thus obtained was purified by silica gel column chromatography using a mixture of chloroform and methanol (volume ratio: 40:1) to yield (±)-2-amino-6-chloro-9-[c-4-hydroxymethylcyclopent-2-en-γ-1-yl]-9H-purine in an amount of 0.19 g. The yield was 72% by mole. The physical properties of the compound obtained were identical to those for a known (±)-2-amino-6-chloro-9-[c-4-hydroxymethylcyclopent-2-en-γ-1-yl]-9H-purine.

The physical properties of the compound thus obtained were as follows:

Melting point: 160° C. to 162° C. $^1$H-NMR (DMSO-d$_6$, 300 MHz) δ (ppm): 1.88(1H, ddd, J=13.7 Hz, 5.5 Hz, 5.5 Hz), 2.62(1H, ddd, J=13.7 Hz, 8.8 Hz, 8.8 Hz), 2.87(1H, m), 3.44(2H, m), 4.78(1H, dd, J=5.2 Hz, 5.2 Hz), 5.44(1H, m), 5.89(1H, m), 6.13(1H, m), 6.86(2H, brs), 7.83(2H, d, J=8.0 Hz), 7.78(2H, d, J=8.0 Hz), 8.02(1H, s) $^{13}$C-NMR (DMSO-d$_6$, 75 MHz, δ ppm)): 160.0, 154.0, 149.7, 141.6, 139.2, 129.6, 123.9, 64.1, 59.5, 48.1, 34.3 MS(EI, m/z): 265, 267 (m$^+$).

COMPARATIVE EXAMPLE 1

Preparation of 2-(N-p-Toluenesulfonyl)-2-azabicyclo[-2.2.1]hept-5-en-3-one

The amount 240 mg (6.0 mmol) of sodium hydride (60% by weight mineral oil solution) was suspended in 50 ml of anhydrous ether, to which 545 mg (50 mmol) of 2-azabicyclo[2.2.1]hept-5-en-3-one was added and stirred for one hour at room temperature. To the resultant mixture 1.14 g (6.0 mmol) of p-toluenesulfonyl chloride was added and stirred overnight at room temperature. After the reaction mixture was filtered to remove solids, the filtrate was distilled to remove the solvent. The residue thus obtained was purified by silica gel column chromatography to yield 605 mg (2.3 mmol) of 2-(N-p-toluenesulfornyl)-2-azabicyclo[2.2.1]hept-5-en-3-one. The yield was 46% by mole.

COMPARATIVE EXAMPLE 2

Preparation of 2-(N-o-Nitrobenzenesulfonyl)-2-azabicyclo[2.2.1]hept-5-en-3-one

The reaction of 1.09 g (10 mmol) of 2-azabicyclo[2.2.1] hept-5-en-3-one with 2.44 g (11 mmol) of o-nitrobenzenesulfonyl chloride was carried out under the same conditions as used in Comparative Example 1. As a result, 1.18 g (4.0 mmol) of 2-(N-o-nitrobenzenesulfonyl)-2-azabicyclo[2.2.1]hept-5-en-3-one was obtained. The yield was 40% by mole.

The present invention being thus described, it will be obvious that the same may be varied in many ways. Such variations are not to be regarded as a departure from the spirit and scope of the present invention, all such modifications as would be obvious to one skilled in the art are intended to be included within the scope of the following claims.

What is claimed is:

1. A method for preparing a bicycloamide derivative represented by the formula (II):

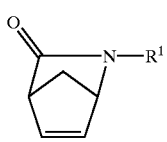

(II)

wherein R$^1$ is an electron withdrawing group having sulfur atom or phosphorus atom directly bonded to the nitrogen atom of the amido group, comprising the step of:

reacting in the presence of an organolithium compound and at a temperature of from −120° C. to 0° C., azabicyclo[2.2.1]hept-5-en-3-one represented by the formula (IV):

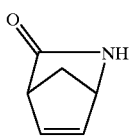
(IV)

with a compound represented by the formula (V):

R¹—X  (V)

wherein $R^1$ is an electron withdrawing group having sulfur atom or phosphorus atom directly bonded to X, and X is a halogen atom.

2. The method according to claim 1, wherein $R^1$ is sulfonyl group.

3. The method according to claim 1, wherein $R^1$ is phosphoryl group.

4. An N-sulfonylbicycloamide derivative represented by the formula (II-1):

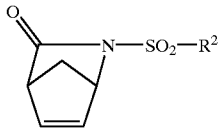
(II-1)

wherein $R^2$ is an aromatic hydrocarbon group which may have a substituent containing one or more atoms except carbon and hydrogen atoms.

5. An N-sulfonylbicycloamide derivative represented by the formula (II-2):

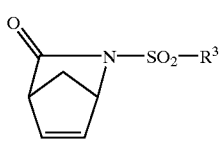
(II-2)

wherein $R^3$ is a substituted or unsubstituted saturated aliphatic hydrocarbon group.

6. An N-phophorylbicycloamide derivative represented by the formula (II-3):

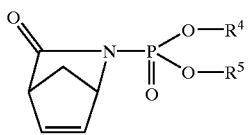
(II-3)

wherein $R^4$ and $R^5$ are independently a substituted or unsubstituted aromatic hydrocarbon group or a substituted or unsubstituted saturated aliphatic hydrocarbon group.

* * * * *